United States Patent [19]
Hammer et al.

[11] Patent Number: 4,894,340
[45] Date of Patent: Jan. 16, 1990

[54] MICROBIAL SULFHYDRYL OXIDASE AND METHOD

[75] Inventors: Frank E. Hammer; Don Scott, both of Schaumburg, Ill.; Fred W. Wagner, Lincoln, Nebr.; Lee Ray, Elk Grove Village, Ill.; Rebecca S. de la Motte, Lincoln, Nebr.

[73] Assignee: Suomen Sokeri Oy, Helsinki, Finland

[21] Appl. No.: 136,723

[22] Filed: Dec. 21, 1987

[51] Int. Cl.$^4$ .............................................. C12N 9/02
[52] U.S. Cl. ................................... 435/189; 435/183; 435/917
[58] Field of Search ...................... 435/183, 68, 189

[56] References Cited
U.S. PATENT DOCUMENTS
4,087,328 5/1978 Swaisgood ............................ 435/68

Primary Examiner—Peter D. Rosenberg
Attorney, Agent, or Firm—Baker & McKenzie

[57] ABSTRACT

A sulfhydryl oxidase, which is a flavor protein, and a method of isloating the same from a culture of the microorganism *Aspergillus niger*. The claimed sulfhydryl oxidase has a molecular weight of about 106,000 and a pH optimum of about 5.5 for oxidation of glutathione in an acetate buffer at 250° C.

14 Claims, 5 Drawing Sheets

Fig.1. Absorbance spectrum of *A.niger* sulfhydryl oxidase

Fig.2. Effect of glutathione on absorbance spectrum of *A.niger* sulfhydryl oxidase

Fig. 3.

Effect of sulfite on absorbance spectrum of A. niger sulfhydryl oxidase

Activity of *A. niger* sulfhydryl oxidase at different pH values

Fig. 8.

Stability of *A. niger* sulfhydryl oxidase at different pH values

◇ ; t = 0
□ ; t = 24 hr.

Fig. 9.
Activity of A.niger sulfhydryl oxidase at different temperatures

Fig. 10.
Stability of A.niger sulfhydryl oxidase at different temperatures

□ ; t = 0
◊ ; t = 4hr.

MICROBIAL SULFHYDRYL OXIDASE AND METHOD

TECHNICAL FIELD

This invention relates to an isolated, microbial derived sulfhydryl oxidase enzyme which is a flavoprotein. One specific aspect of the invention relates to a sulfhydryl oxidase enzyme which is a flavoprotein isolated from *Aspergillus niger* cells. Another specific aspect of the invention relates to stable enzyme preparations of sulfhydryl oxidase, and in addition, to methods for the preparation thereof.

BACKGROUND OF THE INVENTION

The enzyme sulfhydryl oxidase (SHX) catalyzes—in the presence of oxygen—the conversion of thiol compounds to their corresponding disulfides according to the equation:

$$2RSH + O_2 \rightarrow RSSR + H_2O_2$$

Several enzymes with the ability to catalyze this reaction, derived from both mammalian and microbial sources, have been reported in the scientific literature. In 1956, Mandels reported that the spore s of the fungus *Myrothecium varrucaria* contained a sulfhydryl oxidase which catalyzed the oxidation of reduced glutathione (GSH), cysteine and homocysteine with concomitant reduction of $O_2$ to $H_2O_2$. Thiooxidase activity was found in the cell-free culture filtrates of the fungi *Piricularia oryzae* and *Polyporous versicolor* (Neufeld et al., 1950); this oxidase failed to utilize GSH and cysteine as substrates, but oxidized ethylenic linked thiol groups in a wide range of compounds. Aurbach et al. reported that thiooxidase isolated from *P. oryzae* (Aurbach and Jakoby, 1962) was responsible for the metapolyphenol oxidase activity that had been observed in crude *P. oryzae* extracts. In 1975, Olsen isolated a sulfhydryl oxidase from the culture fluid of an organism believed to be *Dactylium dendroides*. This copper metalloenzyme was found in mycelium extracts which also contained galactose oxidase. Olsen reported that the purified sulfhydryl oxidase was capable of reactivating reductively denatured galactose oxidase, as well as protecting the latter enzyme against inactivation by allow molecular weight inhibitor present in the culture fluid.

In 1972, Young and Nimmo reported that an impure preparation of glucose oxidase derived from *Spergillus niger* catalyzed the oxidation of GSH, and speculated that the impure glucose oxidase preparation may contain an enzyme which catalyzes this reaction.

Sulfhydryl oxidases have also been obtained from mammalian sources. In 1975 Janolino and Swaisgood purified an iron-dependent sulfhydryl oxidase from bovine milk which demonstrated activity toward GSH, cysteine, dithiothreitol, 2-mercaptoethanol and reduced ribonuclease A (Janolino and Swaisgood, 1975). The enzyme also restored reduced chymotrypsinogen to a form capable of undergoing conversion to active chymotrypsin (Janolino et al., 1978), and catalyzed the conversion of xanthine dehydrogenase to xanthine oxidase (Clare et al., 1981). Other researchers report that milk extracts from other sources, including human, (Isaacs et al. 1981) as well as kidney homogenates and mammalian pancreas tissue (Clare et al. 1984) exhibit sulfhydryl oxidase activity. Takamuri reported that an enzyme isolated from the skin of young rats catalyzed the oxidation of dithiothreitol, dithioerythritol, D-penicillamine and L-cysteine, although GSH and 2-mercaptoethanol were very poor substrates (Takamuri et al., 1980).

There is no evidence that any of the aforementioned enzymes are flavoproteins. However, a sulfhydryl oxidase activity discovered in rat epididymal fluid (Chang and Morton, 1975) was later demonstrated to be the activity of an FAD-dependent (flavin adenine dinocleotide) enzyme (Ostrowski et al, 1979; Ostrowski and Kistler, 1980). The best substrates for this sulfhydryl oxidase were reported to be dithiothreitol, GSH and cysteine; as in the case of the skin and bovine milk enzymes, this enzyme was capable of reactivating reduced ribonuclease A.

The precise biochemical role of SHX has not yet been determined. Janolino and Swaisgood (1975) suggest that the enzyme may contribute to the formation of disulfide bonds during or after the cellular synthesis of proteins. Chang and Morton (1975) suggest that SHX may protect other enzymes or biological tissues against adventitious reductive damage.

Although the commercial applications of SHX are quite broad and include any context where the oxidation of free sulfhydryl groups to sulfide bonds is desirable, SHX has heretofore been unavailable in quantities of sufficient size and purity for commercial usage. In particular, the expense and availability of mammalian tissue make mammalian sources of SHX unlikely candidates for production of SHX on a large and economically efficient scale. Microbial sources of SHX, on the other hand, could potentially produce SHX on a large scale in a relatively inexpensive and efficient manner. It has now been discovered that *A. niger* produces SHX in sufficient amounts to make it an excellent source of SHX on a commercial scale. *A. niger*-derived SHX is a flavoprotein enzyme which catalyzes the conversion of low molecular weight thiol compounds to their corresponding disulfides and is also capable of accepting protein associated thiol groups as substrates.

SUMMARY OF THE INVENTION

The present invention contemplatee an isolated microbial sulfhydryl oxidase which is a flavoprotein and is characterized by a pH optimum of about 5.5 for the oxidation of glutathione in an acetate buffer at 25° C. The enzyme is further characterized by absorbance maxima at about 442.5 nm, 364.5 nm and 274 nm, and by a molecular weight of about 106,000 as determined by equilibrium sedimentation. The enzyme is constituted by subunits with a molecular weight of about 50,000 to about 55,000 as determined by sodium dodecyl sulfate ("SDS") polyacrylamide gel electrophoresis.

The present invention also contemplates various stable forms of SHX including a stable liquid SHX enzyme preparation with an activity of about 0.3 to about 13 U/mL, a stable enzyme preparation comprising SHX, a buffer and ammonium sulfate sufficient to create an aqueous suspension, and a stable freeze dried SHX enzyme preparation. These enzyme preparations are relatively stable, and can be utilized effectively in contexts where the oxidation of free sulfhydryl to disulfide linkages is desired.

In a method aspect, the present invention provides a means for recovering a flavoprotein SHX from microbial sources by cultivating an SHX producing strain of a mold, recovering SHX from the mold, and purifying the recovered SHX. The recovery of SHX can be accomplished by lysing the cells by enzymatic digestion or other suitable means and precipitating the resulting proteins, or by suspending *A. niger* in brine of sufficient strength to partition the enzyme into the brine solution.

DETAILED DESCRIPTION OF THE PREFERRED EMBODIMENT

A. General

The commercial applications of SHX are quite broad and include any context where the oxidation of free sulfhydryl groups to disulfide bonds is desired. The use of an enzyme in lieu of such non-specific oxidants as hydrogen peroxide, bromates, peracids and the like— has many advantages. The specificity of enzyme catalyzed reactions eliminates the flavor problems non-specific oxidants may cause through the oxidation of other components of a food system. SHX oxidizes under milder conditions than non-specific oxidants which, in food systems, is useful; in food systems, the use of highly acidic, highly basic or high temperature conditions may have an adverse effect on the organoleptic quality of the system. An enzyme catalyzed oxidation will usually have a greater velocity than a non-specific oxidant; for example, SHX may act more quickly on free sulfhydryl groups than a non-specific oxidant.

U.S. Pat. Nos. 4,081,328 and 4,053,644 discuss the use of bovine milk derived SHX to treat Ultra-High Temperature sterilized milk; this treatment removes the burnt flavor from such milk—it is suggested—by oxidizing the free sulfhydryl groups of milk proteins which are liberated during heating. A microbially derived SHX can be used for that purpose as well.

In addition, it has been shown that microbially derived SHX can effectively be used as a dough conditioner to act on free sulfhydryl groups in lieu of non-specific oxidants. Unlike SHX derived from a mammalian (bovine) source which exhibits no beneficial effects in a wheat flour dough [Kaufman et al. Cereal Chem. 64 (3):172-176], the SHX of the present invention derived from a microbial source does improve the rheological properties of dough and provides an improvement in the form and texture of a baked product.

Microbial sources which generate sufficient quantities of SHX—intracellularly and extracellularly—are potential sources for the isolation and production of large scale quantities of SHX. For example, it has been found that *A. niger* is a particularly good source of SHX in recoverable quantities, and that relatively large amounts of SHX can be isolated and purified from cultivated *A. niger*.

*A. niger* is cultivated in any suitable media, for example, a glucose containing media, until a suitable mass of cells is produced. SHX is recovered from the resulting cell mass.

The SHX can be separated from the cell mass by various means. In one such method, the cells are disrupted by the protease ficin, and subjected to ultrafiltration. The protein is subsequently precipitated with an organic solvent such as methanol or acetone. Cells can also be disrupted by other suitable means such as by high pressure disruption. SHX can also be separated from the cell mass by suspending the *A. niger* in a brine solution sufficient to partition the SHX into the brine solution (e.g. 20% (w/v) NaCl). It is suggested that the brine solution creates osmotic pressure sufficient enough to partition the SHX into the brine solution.

The SHX isolated from microbial cells is generally purified by conventional precipitation and chromatographic methods. Such methods include, enter inter alia methanol, ethanol, acetone and ammonium sulfate precipitation and ion exchange and hydroxyapatite chromatography. In particular, acetone precipitation and hydroxyapatite chromatography effectively purify the enzyme by taking advantage of the unusual solubility and stability of the SHX in water acetone mixtures, as compared with the other major protein constituents of the extract.

Two assays have been employed to determine SHX activity. The first assay is based on the depletion of $O_2$ from assay mixtures containing thiol compounds; oxygen depletion is measured polarographically by oxygen electrode techniques. One unit of SHX is defined as that amount of enzyme which would utilize or consume 1 umol of $O_2$ per minute under the conditions of the assay.

The second assay is based on the depletion of reactive sulfhydryl groups as measured by the reaction of residual substrate with DTNB. DTNB reacts with a free sulfhydryl group to yield a species that can be spectrally monitored at 412 nm. This assay can be used to measure SHX activity with respect to both low molecular weight thiols and protein substrates.

The isolated SHX of the present invention exhibits the following characteristics:

1. Molecular Weight

The SHX of the present invention is dimeric with a subunit molecular weight of about 53,000.

Based on SDS polyacrylamide gel electrophoresis, the *A. niger* derived SHX resulted in values of subunit molecular weight of 51,000, 53,000 and 54,000 from gels with acrylamide concentrations of 7.5%, 10% and 12% respectively, giving an average weight of 52,700.

For molecular weight determination, a model V161 Bethesda Research Laboratories vertical slab gel electrophoresis system was used, with all gels and buffers prepared according to the method described by Laemmli (1970). Samples were diluted in a ratio of 2:3 with the sample buffer and boiled for two minutes before application to the gels. After electrophoresis, protein bands were stained by the silver nitrate method of Morissey (1981) or by incubation with a Coommasie brilliant blue staining solution.

The native molecular weight was calculated from sedimentation equilibrium data. Plots of the natural logarithm of fringe displacement versus the square of axial distance from two optical comparator data sets were linear. Molecular weights of 107,400 and 104,200 (average, 106,000) were calculated from their slopes with the equation $M_R = 2RT(\text{slope})/[(1-vp)w^2]$, where w is the angular velocity, p is the solvent density, v the partial specific volume of sulfhydryl oxidase, T the temperature, and R the gas constant. The partial specific volume of sulfhydryl oxidase was taken to be 0.72, as calculated from the enzyme's amino acid composition.

2. Spectral Characteristics of the Isolated SHX

Figure 1:
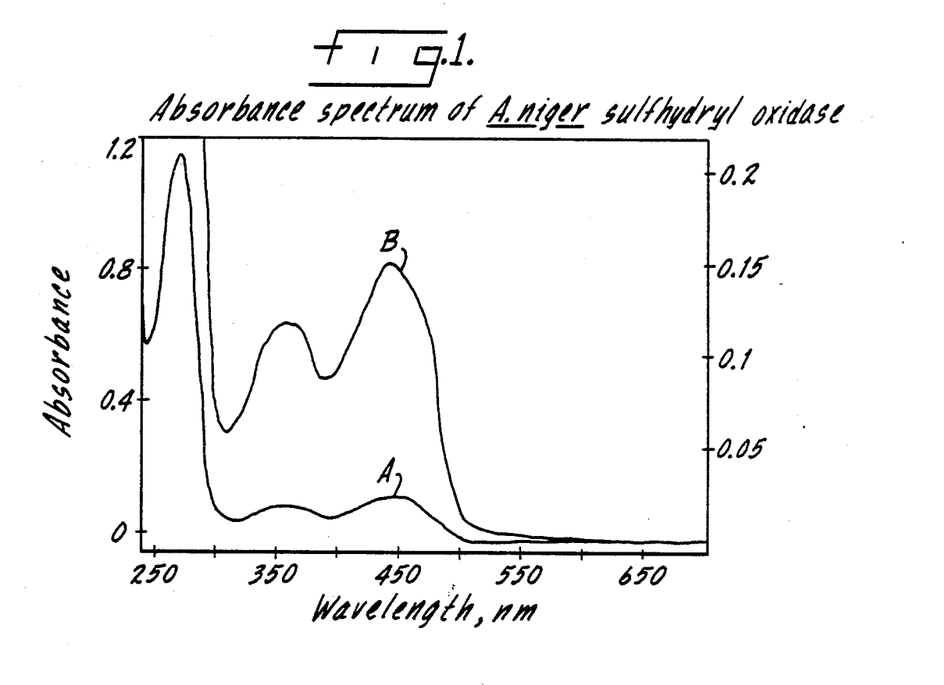
FIG. 1: Absorption spectrum of purified sulfhydryl oxidase in 40 mM sodium acetate, pH 5.5. "A" represents the absorbance spectrum of reduced SHX an "B" represents the spectrum of oxidized SHX.

Spectral analysis of the isolated SHX of the present invention demonstrates that the SHX is a flavoprotein, the first SHX derived from a microbial source identified as such. The UV/visible spectrum of the purified sulfhydryl oxidase had absorbance maxima at 442.5 nm, 364.5 nm and 274 nm in 40 mM sodium acetate, pH 5.5 as shown in FIG. 1. This spectrum is characteristic of a flavoprotein. The visible band had slight shoulders to the left and right of the maximum, at about 415 nm and 460 nm, respectively. The molar absorptivities at the three maxima were determined by recording spectra of enzyme solutions in water, drying the solutions in vacuo over $P_2O_5$, and weighing the residue on a Cahn electrobalance. The $E^{0.1\%}$ values obtained as averages of two determinations with different batches of sulfhydryl oxidase were 1.470, 0.167 and 0.197 $cm^{-1} mg^{-1} mL$ at 274, 364.5 and 442.5 nm, respectively, with no more than a 3% difference between the averaged values. The corresponding molar absorptivities, assuming a molecular weight of 106,000, were $1.56 \times 10^5$, $1.74 \times 10^4$ and $2.09 \times 10^4$ $cm^{-1} M^{-1}$.

Figure 2:
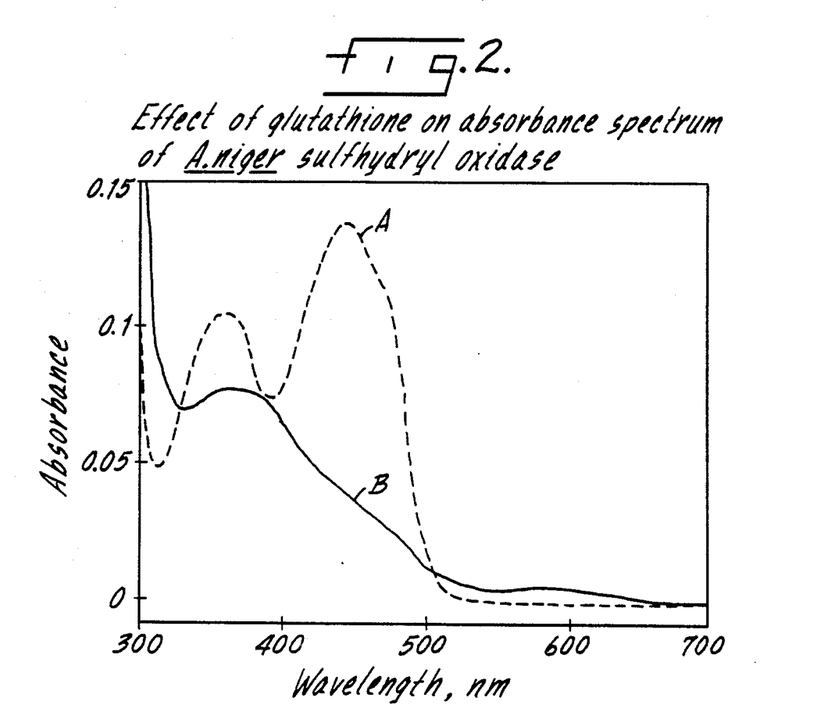
FIG. 2: Absorption spectra of purified sulfhydryl oxidase in 40 mM sodium acetate, pH 5.5 in the absence of (A) and presence of (B) 40 mM GSH.

Addition of 20 mM GSH in sodium acetate (pH 5.5) to sulfhydryl oxidase in the presence of $O_2$ resulted in partial attenuation of the 442.5 nm and 364.5 nm bands, and a slight increase in longwave absorbance as shown in FIG. 2. Spectral changes were not observed when the same amount of GSH was combined with free flavin adenine dinucleotide ("FAD") or flavin mononucleotide ("FMN") under the same conditions. Sodium dithionite reduced both the sulfhydryl oxidase and the free flavin solutions.

Figure 3:
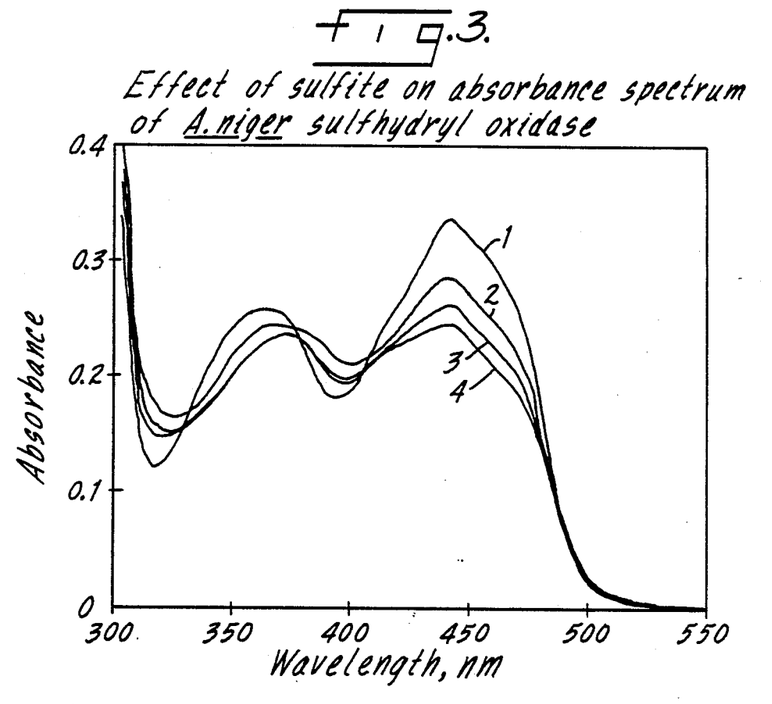
FIG. 3: Absorption spectra of purified sulfhydryl oxidase after reaction with sodium sulfite at pH 6, showing bleaching of the visible bond of SHX spectrum. Each spectrum was recorded 10 minutes after the addition of a small aliquot of sodium sulfite to a cuvette containing 1.8 mg/mL SHX in 50 mM sodium phosphate. Sulfite concentrations after each addition were 0 mM(1), 0.99 mM(2), 2.44 mM(3) and 152 mM(4).

Additional spectral analysis confirms that the SHX of the present invention is a flavoprotein. Most flavin oxidases, but not flavin dehydrogenases, react with sodium sulfite to form a bleached flavin-sulfite complex (Massey et al., 1969). The spectral change incurred by incubation of sulfhydryl oxidase with sodium sulfite at varying concentrations is show in FIG. 3. The dissociation constant $K_d = [SHX][SO_2]/[SHX-SO_2]$ for the sulfhydryl oxidase flavin-sulfite complex was calculated from the first few spectra under the assumption that spectrum 4 in FIG. 3 represented full conversion of the enzyme to the sulfite complex, and that the initial excess of sulfite was so large that its concentration was essentially unchanged at equilibrium. The first assumption was justified by the fact that spectrum 4 (152.8 mM sulfite) was identical with the spectrum recorded when the sulfite concentration was just 42.8 mM (not shown). These calculations gave values of $3.04 \times 10^{-3}$ and $2.95 \times 10^{-3}$ for $K_d$, from spectra 1 and 2, respectively.

3. Flavin Analysis and Stoichiometry

*A. niger* sulfhydryl oxidase exhibited the reactivity with sulfite which is characteristic of most flavin oxidases, but not flavin dehydrogenases, and is believed to be correlated directly with the enzyme's ability to undergo oxidation by molecular oxygen (Massey et al., 1969). The dissociation constant for the sulfhydryl oxidase flavin-sulfite complex was on the same order of magnitude as those reported by Massey et al. (1969) for D-amino acid oxidase and oxynitrilase, but the spectral changes accompanying sulfite binding to sulfhydryl oxidase were much less extreme than those seen for any of the reactive enzymes investigated by these workers. The absorbance of sulfhydryl oxidase at 442.5 nm was only 25% reduced by complete conversion to the sulfite complex, and the 364.5 nm band showed a shift rather than an attenuation. It is notable that the flavin sulfhydryl oxidase from rat epididymal fluid failed to react with sulfite at concentrations as high as 0.1M (Ostrowski and Kistler, 1980) as judged by the absence of changes in the enzyme's visible spectrum.

Figure 4:
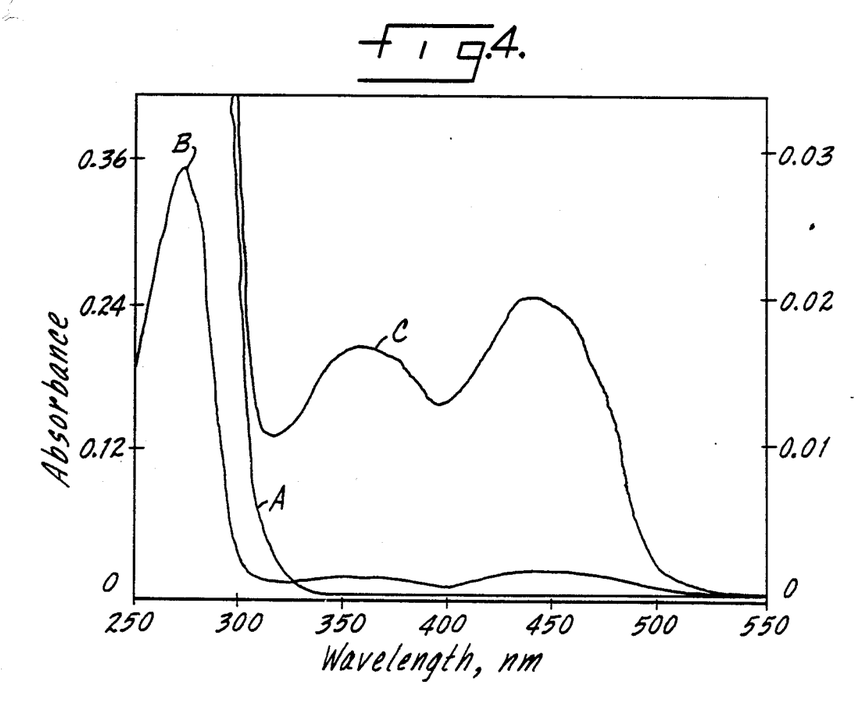
FIG. 4; The spectrum of sulfhydryl oxidase (A) after removal of the native flavin moiety by treatment with 5M guanidine HCl, and (B) after incubation of the apoenzyme with excess FAD at pH 7.0 for approximately 14 hours. Spectrum (C) shows detail of spectrum (B).

Treatment of the enzyme with guanidine HCl followed by particle exclusion chromatography resulted in complete resolution of the flavin component and the protein, as was indicated by the failure of the visible and near UV absorbance bands to appear in the spectrum of the recovered protein (FIG. 4). Flavin-depleted preparations did not have measurable activity toward GSH. Incubation of the apoenzyme with excess FAD at neutral pH, followed by gel filtration for removal of unbound flavin, restored activity to the enzyme, and resulted in recovery of the spectral bands at 442.5 nm and 364.5 nm (FIG. 4). The reconstitution was incomplete, but restored activity was essentially proportional to restored flavin, as can be seen by comparing the specific activity and the ratio $A_{442.5}/A_{274}$ of the reactivated enzyme to those of the native control as shown in Table I set forth below. Incubation with FAD for times longer than 14 hours failed to change either of these parameters further. Incubation of the apooxidase with excess FMN under a variety of conditions (pH values ranging from 3 to 9 in the presence of various buffer salts) did not result in any detectable restoration of activity toward GSH under standard assay conditions.

TABLE I

Reconsitutition of Sulfhydryl Apooxidase[a]

| | Activity units/mg | Activity % | $A_{442.5}/A_{274}$ | FAD bound % |
|---|---|---|---|---|
| Native SHX | 9.7 | 100 | 0.112 | 100 |
| apoSHX | 0.0 | 0 | 0.0 | 0 |
| apoSHX + FAD | 6.3 | 65 | 0.067 | 60 |
| apoSHX + FMN | 0.0 | 0 | —[b] | —[b] |

[a]Activity and flavin binding parameters for sulfhydryl oxidase. The ratio $A_{442.5}/A_{274}$ was taken as a measure of flavin binding, with the assumption that the native and apo forms of the enzyme had the same molar absorptivities at 274 nm.
[b]Not determined.

Fluorometric analysis of the flavin constituent gave results which are summarized in Table II below. At values of pH below 3, FAD exhibits strong fluorescence at 530 nm when excited at 450 nm. At neutral to basic pH, FAD is weakly fluorescent owing to quenching by its adenine moiety. FMN and other nonadenylated flavins, on the other hand, fluoresce strongly under both conditions of pH (Bessey et al., 1949); Cerletti and Siliprandi, 1958). Thus the ratio of fluorescence at basic pH to that at acidic pH distinguishes adenylated from nonadenylated flavins. The data in Table II shows that the flavin preparation method, which involved denaturation of the sulfhydryl oxidase by boiling, resulted in the liberation of a flavin with fluorometric characteristics identical to those of FAD, whereas the other two methods gave a nonadenylated flavin as their products. When the isolated flavins were recombined with sulfhydryl apooxidase, only the product of treatment by boiling was capable of restoring activity to the enzyme.

TABLE II

Analysis of Flavin Resolved from Sulfhydryl Oxidase[a]

| Method of Resolution | $F_{base}/F_{acid}$ | Activity units/mL[b] |
|---|---|---|
| Boiling | 0.21 | 0.35 |
| Trichloroacetic acid treatment | 1.47 | 0.0 |
| Guanidine HCl treatment | 1.48 | 0.0 |
| Authentic FAD | 0.23 | 0.58 |
| Authentic FMN | 1.38 | 0.0 |

[a]Samples of flavin resolved from sulfhydryl oxidase were prepared and subjected to fluorometric analysis as described in the text. The quantities $F_{base}$ and $F_{acid}$ are proportional to the fluorescence of the flavin solutions at pH 7.7 and 2.6, respectively. Concentrations of flavin standards and flavin samples were not identical.
[b]Activities are those of sulfhydryl apooxidase samples after 14 hours incubation at 0° C. in the presence of resolved flavins or standards.

The flavin to protein stoichiometry of sulfhydryl oxidase was established to be 1.68 moles FAD per mole of enzyme (m.w. about 106,000) by recording the spectrum of a known concentration of native sulfhydryl oxidase, liberating the flavin by boiling, and recording the spectrum of the boiled solution. These experiments showed the enzyme to be slightly hyperchromic relative to free FAD; the molar absorptivity of the bound flavin was 12,4000 cm$^{-1}$ M$^{-1}$, as compared to 11,300 cm$^{-1}$ M$^{-1}$ for free FAD.

Since flavin oxidases containing essential metal ions are known to exist, sulfhydryl oxidase was examined for changes in activity upon treatment with the chelating agents. No activity decreases were observed when the enzyme was combined with and assayed in he presence of either 1 mM o-phenanthroline or 1 mM 8-hydroxyquinoline in 0.05M phosphate buffer, pH 7.0, even after overnight incubation with the chelating agents.

Other evidence supports the conclusion that *A. niger* SHX is a flavoprotein. By treating *A. niger* SHX with 5M guanidine HCl, an apoenzyme was prepared; following molecular exclusion chromatography discreet flavin and protein component spectrum resulted. In addition, a SHX preparation depleted of flavin showed no measurable reactivity with GSH, although incubation of the flavin-depleted apoenzyme with excess FAD restored enzymatic activity, and restored the spectral bands at 442.5 nm and 364.5 nm.

Incubation overnight at pH 3.0 failed to destroy *A. niger* sulfhydryl oxidase activity. The acid stability of the enzyme may be related to the fact that the flavin moiety is difficult to remove from the enzyme without irreversible protein denaturation. Acid ammonium sulfate precipitation, extended dialysis against high concentrations of KBr at low pH, incubation with 8M urea and treatment with various chaotropic salts all failed to give any resolution of flavin from protein. In addition, the fluorometric data suggest that the guanidine HCl method used to prepare the apoenzyme was effective, at least in part, through its ability to convert the native adenylated flavin to an unadenylated form.

4. Kinetic Properties and Substrate Specificity

Figure 5:
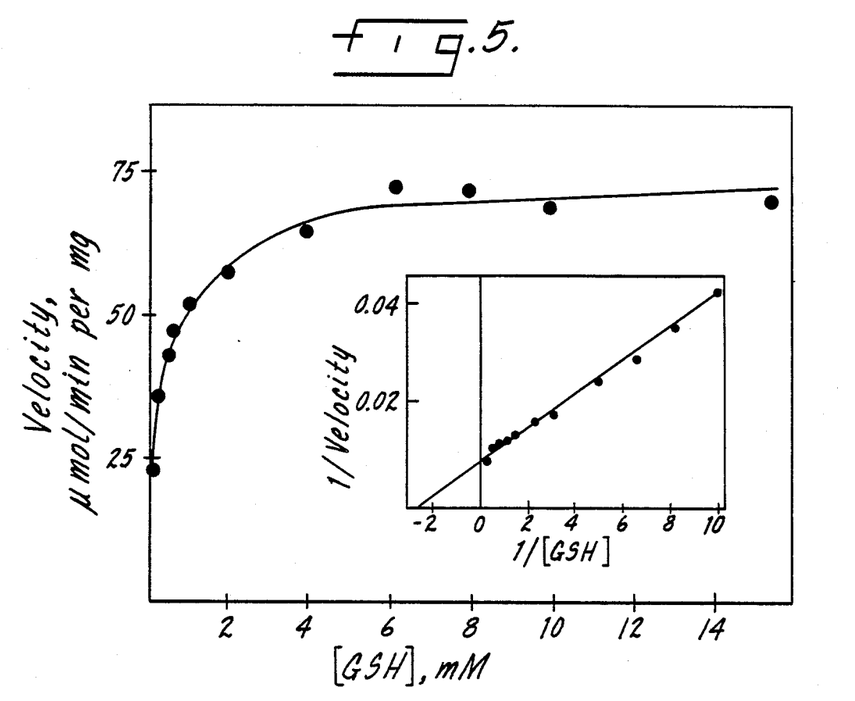
FIG. 5: Activity of SHX as a function of GSH concentration. Assays were performed at pH 5.5 and 25° C. in 40 mM sodium acetate, with 0.166 mg/mL SHX. Velocity is expressed as activity units per mg of enzyme.

*A. niger* cell extract and the purified enzyme both depleted O$_2$ from solutions containing various thiol compounds. Rates of O$_2$ depletion by the purified enzyme were measured at selected concentrations of GSH, cysteine, dithiothreitol and 2-mercapto-ethanol. Double reciprocal plots prepared for each substrate tested were linear over a substrate concentration range of at least one order of magnitude. FIG. 5 shows the saturation curve obtained when the substrate was GSH, with the double reciprocal plot inset. Kinetic constants were calculated from the double reciprocal plot by linear regression fitting of the data points. The values obtained for each substrate are given in Table III a set forth below.

TABLE III

Kinetic Constants for Various Substrates[a]

| Substrate | $K_{m\ (app)}$ (mM) | $k_{cat\ (app)}$ (min$^{-1}$) | $\dfrac{k_{cat\ (app)}}{K_{m\ (app)}}$ (min$^{-1}$M$^{-1}$) |
|---|---|---|---|
| Glutathione | 0.3 | 7875 | 26,000 |
| Cysteine | 43.0 | 9975 | 230 |
| Dithiothreitol | 66.0 | 7140 | 110 |
| 2-Mercaptoethanol | 340 | 8715 | 26 |

[a]Assays were performed polargraphically using glutathione as described in the text. Protein concentrations were calculated from the absorbance of the enzyme solutions at 274 nm.

Sulfhydryl oxidase had maximal and nearly constant activity between pH 5.0 and 5.5 when GSH was the substrate. The enzyme had no activity at pH 2.5, and very little at pH 10.0. When sulfhydryl oxidase was incubated for 24 hours at various values of pH but assayed under the standard conditions (pH 5.5), activity remained constant while the pH was between 3.0 and 8.5 in the incubation mixtures, but declined sharply in solutions with pH values more extreme than these.

The enzyme was tested for activity toward substrates of other known oxidases, including D-glucose, D-fructose, L-lysine, D-lysine, benzylamine, xanthine, putrescine, catechol, nicotinamide adenine dinucleotide (reduced) ("NADH") and nicotinamide adenine dinucleotide phosphate (reduced) ("NADPH"). In each case, the enzyme failed to stimulate from assay mixtures containing the test compounds at concentrations of 10 mM in 40 mM sodium acetate at pH 5.5. In other tests, NAD and NADP did not act as electron acceptors in the presence of sulfhydryl oxidase and 4 mM GSH, as indicated by the lack of measurable increase in absorbance of these solutions at 340 nm.

Figure 6:
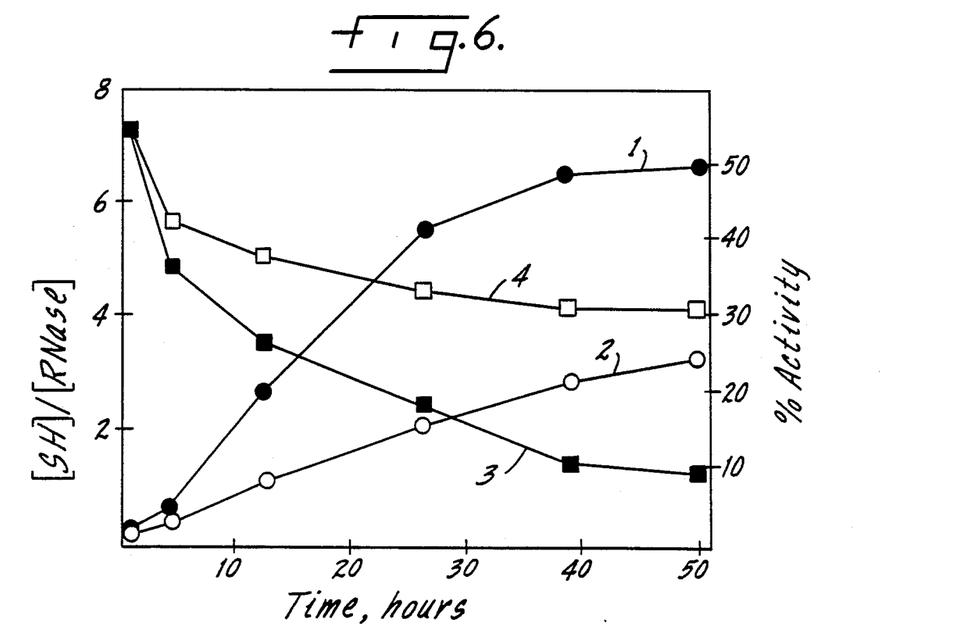
FIG. 6: Reactivation of reductively denatured ribonuclease A. Reactive SHX content was measured by reaction with 5,5' dithiobis (2-nitrobenzoic acid) ("DTNB") in presence and absence of 0.11 mg/mL SHX. Restoration of ribonuclease activity in the presence and absence of SHX was measured by recording the increase in absorbance at 258 nm of a yeast RNA solution. Line 1 represents ribonuclease activity at 258 nm in presence of SHX and Line 2 represents ribonuclease activity at 258 nm in the absence of SHX. Line 3 represents the amount of DTNB present over time in the presence of SHX and Line 4 represents the amount of DTNB present over time in the absence of SHX.

The rate of reactivation of reductively denatured ribonuclease A was enhanced by the presence of sulfhydryl oxidase as shown in FIG. 6, which indicated that the enzyme is capable of catalyzing the oxidation of protein-associated thiol groups. Reactive sulfhydryl content of the ribonuclease, which represented 94% of complete reduction. After 50 hours of incubation with the highest concentration of sulfhydryl oxidase, in which experiment ribonuclease was present in 31.9-fold molar excess, the ribonuclease preparation had retained 50% of its native activity. In the same period the control mixture containing acetate buffer in place of sulfhydryl oxidase solution regained only 24% of its native activity. Reactive sulfhydryl content declined 1.4 moles SH per mole ribonuclease in the presence of the sulfhydryl oxidase, but only to 4.2 moles SH per mole ribonuclease in the control mixture. Other incubation mixtures containing one-half and one-fourth this quantity of sulfhydryl oxidase exhibited smaller degrees of ribonuclease reactivation.

The ability of *A. niger* SHX to enhance the reactivation of reductively denatured ribonuclease A indicates that protein associated thiol groups are potential substrates of the enzyme. A reductively denatured ribonuclease A solution demonstrated enhanced ability to regain native activity after incubation with *A. niger* SHX compared to a control mixture of the reductively denatured protein.

5. Product and Stoichiometry Determination

The oxidized product of the reaction with GSH as substrate was established to be glutathione disulfide by the incorporation of a GSH solution preincubated with the sulfhydryl oxidase into an assay for the NADPH-coupled enzyme glutathione reductase. A significant decrease in absorbance at 340 nm was recorded when a preincubation mixture containing GSH and native sulfhydryl oxidase was combined with a solution of NADPH and glutathione reductase; no such decrease occurred when boiled sulfhydryl oxidase solution was substituted for the native enzyme, or when active sulfhydryl oxidase was combined with GSSG and NADPH in the absence of glutathione reductase.

Reduction of $O_2$ in the course of the reaction resulted in production of $H_2O_2$, as was shown by the coupling of the GSH oxidation with a peroxidase colorimetric system. Quantitative determinations of this type, in conjunction with assays for residual reactive sulfhydryl groups in enzyme/GSH solutions, gave a ratio of GSH consumed to $H_2O_2$ produced of approximately 2:1. Results from three independent determinations were $0.758 \pm 0.025$ mmoles GSH depleted and $0.412 \pm 0.013$ mmoles $H_2O_2$ produced, for a ratio of GSH depleted to $H_2O_2$ produced of $1.84 \pm 0.06$.

As noted, the molecular weight determinations performed in this study suggest that *A. niger* sulfhydryl oxidase is dimeric, with a subunit molecular weight of about 53,000. It is therefore reasonable to expect that the flavin protein stoichiometry should be integral with respect to this molecular weight. However, the data pertaining to flavin stoichiometry gave a value of 1.68 moles of FAD per mole of protein, or 0.84 FAD molecules per subunit. There are several possible reasons for this: the apoenzyme may be incompletely assembled into holoenzyme by the organism, the flavin moiety may be a derivative of FAD, rather than FAD itself, or the molecular weight estimate may be prejudiced by the assumption that 0.72 represents a reasonable partial specific volume. Macromolecular carbohydrates, in general, have lower partial specific volumes than do proteins (Smith, 1967) and it is well known that SDS polyacrylamide gel electrophoresis may fail to give good estimates of the molecular weights of glycoproteins.

We have found that double reciprocal plots of saturation data when GSH is the substrate for the purified enzyme are linear when the substrate concentrations lie between 0.2 and 20 mM. An examination of the kinetic equations describing the velocity of an enzyme which couples two identical substrate molecules shows that in most mechanistic interpretations, double reciprocal plots should be parabolic or hyperbolic rather than linear, but will approximate linearity (over the substrate concentration ranges employed) if there are two substrate binding events which have very different apparent Michaelis constants. The linearity observed in these studies may indicate that the substrates tested here are high efficiency substrates with respect to one binding event, but low efficiency substrates with respect to another binding event.

6. SHX Activity at Different pH and Temperature Ranges

Figure 7:
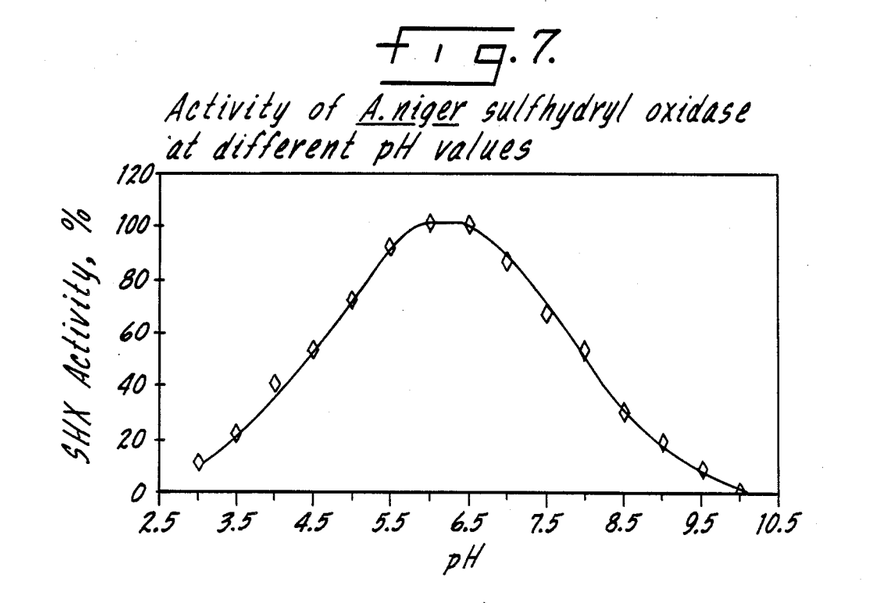
FIG. 7: Activity of *A. niger* sulfhydryl oxidase at different pH values.

*A. niger* SHX exhibits activity over a broad range of pH values with a pH optimum of between pH of about 5.0 and of about 5.5 when the substrate is GSH in a sodium acetate buffer. FIG. 7 sets forth the activity of the SHX of the present invention at pH values of 3.0 to 10.0 using GSH as the substrate. This is in contrast to a pH optimum of 7.0 for bovine SHX for the same substrate.

It has also been found that the pH optimum for *A. niger* varies depending on the buffer; the pH optimum for *A. niger* SHX in a sodium phosphate buffer is in the range of about 6 to about 7.

Figure 8:
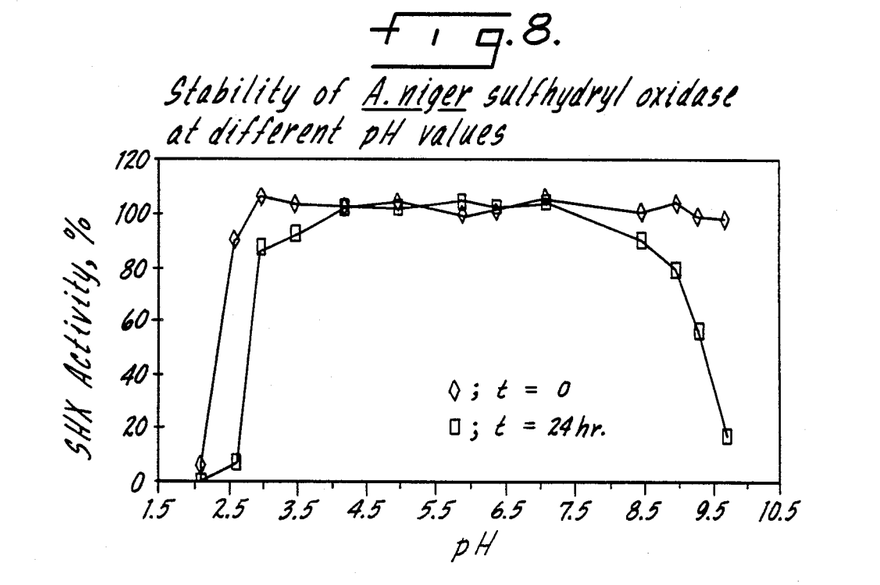
FIG. 8: Stability of *A. niger* sulfhydryl oxidase at different pH values.

The enzyme is relatively stable as incubation of *A. niger* SHX at pH levels of about 3.0 to about 8.5 did not decrease the activity levels when assayed at pH 5.5 as demonstrated in FIG. 8. The stability of SHX under acidic conditions may be related to removal of the flavin moiety. Incubation at more extreme pH levels did result in sharp declines in activity.

Figure 9:
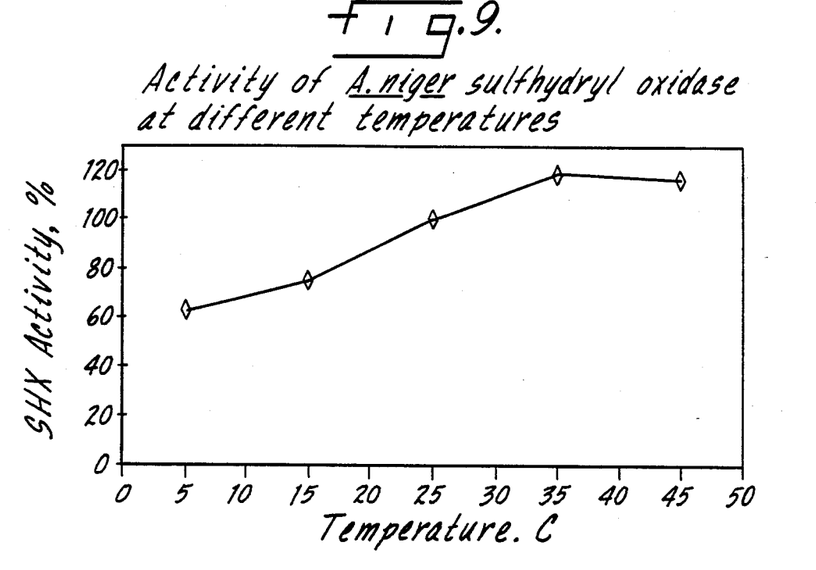
FIG. 9: Activity of *A. niger* sulfhydryl oxidase at different temperatures.
Figure 10:
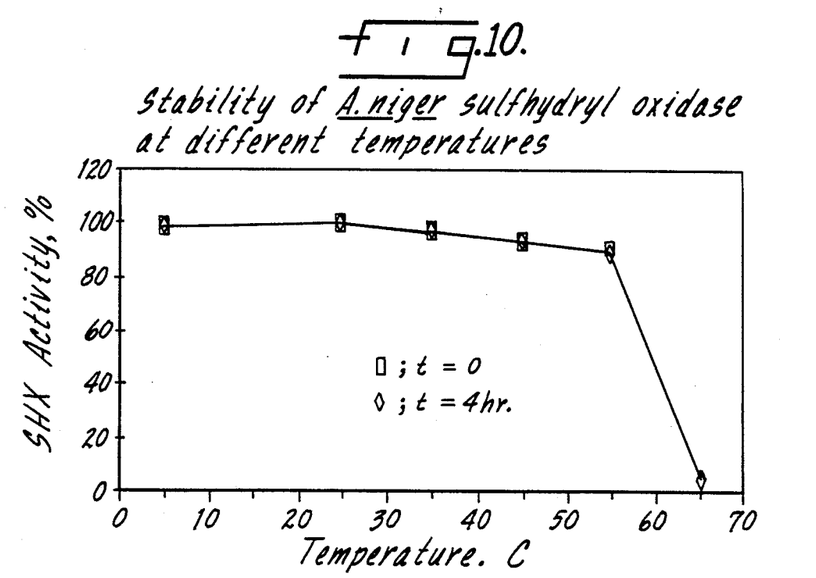
FIG. 10: Stability of *A. niger* sulfhydryl oxidase at different temperatures.

The SHX of the present invention exhibited maximum activity (with GSH as a substrate) at temperatures in the range of about 30° C. to about 45° C., as shown by FIG. 9. As is typical of most enzymes, SHX incubated at various temperatures showed fairly constant activity when the incubation temperature was less than about 5° C. Temperatures above 55° C. denature and inactivate the enzyme as shown by FIG. 10.

B. Experimental Example 1

Cultivation of *A. Niger*

*A. niger* cells were cultivated in a media consisting of:

| A. niger cells were cultivated in a media consisting of: | | |
|---|---|---|
| glucose | 240 | g/L |
| diammonium hydrogen phosphate | 0.42 | g/L |
| urea | 0.11 | g/L |
| potassium dihydrogen phosphate | 0.20 | g/L |
| magnesium sulfate heptahydrate | 0.17 | g/L |

-continued

| A. niger cells were cultivated in a media consisting of: | |
|---|---|
| corn steep liquor<br>pH adjusted with sulfuric acid<br>before sterilization<br>from 6.5 to 4.5 | 3.7 mL |

Growth continued until a suitable mass of cells were produced. During fermentation, the pH was readjusted upward with sodium hydroxide as gluconic acid was produced thus forming sodium gluconate.

EXAMPLE 2

Separation of A. Niger SHX

A. niger cells cultivated as in Example 1 were collected and lysed with about 50–200 mg/L of ficin. The lysed cells were separated by filtration and the filtrate was subjected to ultra filtration using an Amicon DC10L unit or equivalent operated as per the manufacturer's instructions and having a 30,000 MW cut-off hollow fiber cartridge. The ultra filtration step reduced the volume of the filtrate to about 5 to 20% of the original volume. NaCl was added to a final concentration of 20 to 24% and the pH maintained at 5.0 to 5.5 with a 50 mM sodium citrate 50 mM sodium phosphate buffer.

EXAMPLE 3

Purification of A. Niger SHX Using Organic Solvents and Ion Exchange Resins Sulfhydryl oxidase was purified from the semi-purified extract of A. niger, prepared as described in example 2. The initial steps include fractionation with an organic solvent such as methanol or acetone; the purification of SHX is then completed by column chromatography on an anion exchange resin such as DEAE cellulose (Whatman DE-52) or DEAE Trisacryl M (LKB).

In a typical fractionation with methanol, the semipurified SHX extract (as prepared in Example 2) is adjusted to low ionic strength, typically less than 10 mS/cm, and preferably below about 4 mS/cm, in a solution containing 25 mM sodium acetate, pH 5.5. The solution (typically 900–10000 ml at about 8 to about 80 U SHX/mL) is cooled to about 4° C. and methanol at 4° C. is added to give a final concentration of 53% (v/v). The pH of the solution is then adjusted to pH 4.2 by adding an appropriate acid (e.g. citric acid) and the solution is allowed to stand at least 1 hour at 4° C. The precipitated material is then sedimented by centrifugation, e.g. at least 5,000 g for 30 minutes or preferably 16,000 g for 20-30 minutes at 4° C. The fluid is decanted and the methanol is removed by evaporation under vacuum on a rotary evaporator (e.g. Rotovap apparatus) or other suitable means at 30°–40° C.

In a typical fractionation with acetone, the semi-purified SHX extract (as prepared in Example 2) is adjusted to a low ionic strength and pH as discussed above, and cooled. Acetone at 4° C. to −20° C. is added to the cooled enzyme solution to give a final concentration of 40 to 47% (v/v), preferably 40%. The pH of the solution is adjusted to pH 4.0–4.2 by adding an appropriate acid (e.g. citric acid). The solution is allowed to stand and the acetone is removed by evaporation under vacuum on a rotary evaporator (e.g. Rotovap apparatus) or other suitable means at about 30°–40° C.

After removing the organic solvent, sulfhydryl oxidase is precipitated from solution by adding solid ammonium sulfate to give 85% saturation. After the ammonium sulfate has dissolved, the solution is stored at 4° C. for at least 1 hour, preferably at least 4 hours, and then centrifuged, e.g. at 5,000g for about 30 minutes, preferably 18,000 g for 20-30 minutes. The supernatant liquid is discarded and the SHX bearing precipitate is dissolved in a small amount of 40 mM sodium acetate with a pH of about 5.5. The resulting SHX solution is dialyzed extensively against a large excess of the same buffer, e.g. against two changes of about 100-fold excess for at least 4–6 hours each. The dialyzed sample is centrifuged as described above and the fluid is decanted for chromatography.

The SHX in the dialyzed solution is purified by chromatography on anion exchange resin, e.g. DEAE cellulose (Whatman DE-52) or DEAE Trisacryl M (LKB). A column of the resin, typically 2.5× about 30 cm, is equilibrated with 40 mM sodium acetate at a pH of about 5.5 and a temperature of about 4° C. The dialyzed solution is next applied to the column followed by an initial wash with additional equilibration buffer. When essentially free of loosely bound protein, the SHX is eluted with a linear gradient of 40 to 500 mM sodium acetate, pH 5.5. Alternatively, SHX can be eluted with a linear gradient of 40 to 300 mM sodium acetate, pH 5.5 or with 150 mM sodium acetate, pH 5.5. The latter modification is useful for samples with greater amounts of glucose oxidase as it provides a better separation of SHX and glucose oxidase.

An alternative chromatographic purification utilizes the SHX bearing precipitate of the addition of ammonium sulfate as described above. The precipitation is redissolved in 25 mM sodium acetate, pH 4.6, and extensively dialyzed against a large excess of the same buffer, e.g., against two changes of about 100 fold excess for at least 4–6 hours each. The dialyzed sample is centrifuged as described above and the fluid is decanted for chromatography.

The SHX in the dialyzed solution is purified on anion exchange resin, e.g., DEAE cellulose (Whatman DE-52) or DEAE Trisacryl M(LKB). A column as described above is equilibrated with 25mM sodium acetate, pH 4.9. After loosely bound contaminating protein is eluted using the same buffer, SHX is eluted using 60 mM sodium in 25 mM sodium acetate, pH 4.9 or a linear gradient of 0 to 100 mM sodium chloride or 0 to 200 mM sodium chloride in 25 mM sodium acetate, pH 4.9. Depending on the exact nature and quantity of contaminating protein, these alternatives may provide better results, typically resulting in highly purified SHX with less than 1% glucose oxidase (on an activity basis).

The fractions highest in SHX activity are combined and concentrated as necessary using an Amicon PM-10 ultrafiltration membrane. The concentrated material can be either precipitated with ammonium sulfate at 85% saturation and stored or dialyzed against 5 mM sodium citrate, pH 5.5, and freeze-dried, or stored under other stable conditions. The enzyme can also be stored as a liquid preparation with an activity of at least 3 U/ml, with a preferred range of about 3 U/mL to 13 U/mL.

Example 4

Purification of A. Niqer SHX Using Methanol and Hydroxyapatite

A. niger mycelia as cultivated in Example 2 were suspended as a viscous suspension in 20% (w/v) NaCl. Cells were separated from the brine by vacuum filtration through Micracloth. This procedure yielded 850 to 950 mL of brine per liter of cell suspension. Various attempts to disrupt the recovered cells revealed that most of the sulfhydryl oxidase activity had been partitioned into the brine prior to its separation from the cells, so the enzyme was purified from the yellow-brown brine extract, and the cells were discarded after filtration.

Proteins were separated from the brine filtrate by precipitation with methanol. In a typical precipitation, 270 mL of brine filtrate at 0° C. was mixed with 180 mL (40% v/v) of technical-grade methanol at −20° C. This mixture was maintained in an ice bath for 30 minutes, then was centrifuged for 20 minutes at 16,000×g to provide pellets and a yellow supernatant fluid. The pellets were discarded and the supernatant fluid was combined with 450 mL (total 70% v/v) of methanol at −20° C. The resulting suspension was maintained for 10 minutes in an ice bath, then was centrifuged for 15 minutes at 16,300×g. The yellow supernatant fluid was discarded and the centrifuge bottles were shaken and inverted to remove as much of the residual fluid present as possible. A total of 80 mL of 40 mM sodium acetate, pH 5.5, was added to the centrifuge bottles, and the obtained pellets were gently disrupted and allowed to soak in the buffer overnight at 4° C. Undissolved material was then dispersed into the liquor, and the suspension was centrifuged again for 10 minutes at 27,000×g. The supernatant fluid was collected, and solid ammonium sulfate was added to 85% of saturation at 25° C. The suspension thus obtained was stored at 4° C. for at least a month without any observed significant loss of sulfhydryl oxidase activity.

For further purification, six batches of the ammonium sulfate-precipitated enzyme were combined and centrifuged at 4° C. for 15 minutes at 16,300×g. The sedimented material was dissolved in 10 mM sodium citrate, pH 4.0, so that the total volume of the solution did not exceed 40 mL. This solution was desalted by passage over a 2.5×35 cm Sephadex G-25 column equilibrated and eluted with 10 mM sodium citrate buffer, pH 4.0. The protein-containing peak was collected. Sufficient acetone at −20° C. was added to the collected protein to make the solution 30% (v/v) in acetone. This mixture was allowed to stand on ice for 15 minutes, then was centrifuged for 15 minutes at 27,000×g. A dark brown pellet was obtained and discarded, and the yellow supernatant fluid present was passed in its entirety over a hydroxylapatite (Bio-Rad DNA Grade BioGel HTP) bed packed in a 50 mL syringe barrel plugged at the bottom with glass wool. All colored material in the acetone supernatant bound to the hydroxylapatite. The column was washed successively with approximately two volumes of each of the following: 30% acetone/70% 10 mM sodium citrate buffer, pH 4.0; 25% acetone/75% buffer; and 20% acetone/80% buffer. Finally, the hydroxylapaptite was washed with 15% acetone/85% buffer until the eluate was colorless. All solvents were prepared by combination of degassed buffer with acetone which had been vacuum filtered through a Millipore GVWP membrane, and were allowed to stand at 4° C. for several hours prior to the chromatography. The hydroxylapatite was suspended in the acetone-free buffer and the suspension was degassed before the material was packed in the syringe barrel. The column was equilibrated in the 30% acetone/70% buffer mixture immediately before the sample was applied. These measures were required to prevent the formation of gas bubbles in the column during loading and elution. All operations were performed at 4° C. Flow rates were not greater than 1 mL/minute during any step in the chromatography.

Most of the observed sulfhydryl oxidase activity was resident in the material eluted with the last solvent. This bright yellow solution was concentrated to about 40 mL by pressure filtration in a stirred cell over an Amicon YM-10 membrane, if necessary, and solvent exchange was accomplished by passage of the solution through a 2.5 by 35 cm Sephadex G-25 column equilibrated and eluted with 40 mM acetate, pH 5.5. The protein-containing peak was collected and applied to a 2.5×8 cm column of Whatman DE-52 DEAE cellulose which had previously been equilibrated in 40 mM acetate buffer, pH 5.5. The column was developed with a 500 mM linear gradient of increasing total acetate concentration (40 mM to 300 mM), pH 5.5.

Fractions containing 8 mL each were collected after initiation of the acetate gradient, and those exhibiting the highest sulfhydryl oxidase activities (approximately fractions 8 through 18) were pooled. The purified product was stored at 4° C. as an 85% ammonium sulfate suspension. For later experiments, aliquots of the suspension were removed in the required amounts, centrifuged, dissolved in the desired buffer, and desalted by passage over a Pharmacia PD-10 (Sephadex G-25) column equilibrated in the same buffer.

TABLE IV

Purification of Sulfhydryl Oxidase

| Fraction | Volume mL | Activity units | Specific Activity U/mg protein | Recovery % |
|---|---|---|---|---|
| A. Crude cell filtrate | 1620 | 7857 | 7.5 | 100 |
| B. Methanol precipitate | 440 | 7920 | 8.0 | 101 |
| C. (NH$_4$)$_2$SO$_4$ pellet | 50 | 6150 | 8.4 | 78 |
| D. G-25 eluate | 56 | 6160 | 9.4 | 78 |
| E. Acetone Supernatant | 80 | 8320 | — | 106 |
| F. Hydroxylapatite eluate | 80 | 6160 | — | 78 |
| G. G-25 eluate | 59 | 3245 | 73.2 | 41 |
| H. DEAE cellulose eluate | 95 | 2812 | 114.6[a] | 36 |

[a]The Bradford reaction was found to underestimate of sulfhydryl oxidase concentration in pure preparations; the specific activity of the purified material was 73.4, as calculated from its molar absorptivity at 274 nm.

EXAMPLE 5

Assays for Sulfhydryl Oxidase Activity

Determination of sulfhydryl oxidase activity was based upon depletion of $O_2$ from assay mixtures containing thiol compounds, as measured with a Yellow Springs Instruments oxygen monitor (model 500) equipped with a polarographic Clark-type electrodes. In a typical assay, 2.9 mL of a mixture consisting of a thiol compound in an appropriate buffer was equilibrated with stirring to 25° C. After the vial was sealed with the electrode, a volume of 0.1 mL of enzyme solution was injected into the assay mixture. The rate of oxygen depletion was constant during the first 30 seconds of the assay; thus, the initial rate of $O_2$ depletion was taken to be sulfhydryl oxidase activity under the prevailing conditions. One unit of sulfhydryl oxidase was defined as that amount of enzyme which would deplete 1 umole of $O_2$ per minute under the conditions of the assay. Unless otherwise indicated, the assay mixture contained 8 mM GSH in 40 mM acetate buffer, pH 5.5, at 25° C.

In some instances, depletion of reactive sulfhydryl groups from sulfhydryl oxidase assay mixtures was measured by reaction of residual substrate with DTNB. Specifically, an appropriate volume of assay mixture was diluted ten-fold with 0.2 mM DTNB in 20 mM sodium phosphate buffer at pH 8.0. This solution was maintained at room temperature for at least two minutes, after which time its absorbance at 412 nm was measured against a blank prepared by substituting buffer for the sulfhydryl-containing solution in the assay procedure. Sulfhydryl concentration was calculated from the molar absorptivity of the liberated thiolate anion at 412 nm, 13,600 $M^{-1}$ $cm^{-1}$ (Ellman, 1959), in the case of protein substrates, or by comparison to a standard curve prepared from solutions of known sulfhydryl content, in the case of GSH.

EXAMPLE 6

Amino Acid and Carbohydrate Studies

1. Amino Acid Analysis

Vapor-phase acid hydrolysis of sulfhydryl oxidase (5.25 ug per sample) was performed in a vial fitted with a teflon valve according to the procedure of Hirs (1967a) for 24, 48 and 72 hours. Amino acid standards (Pierce, Standard H) were also subjected to the hydrolysis procedure for each of the times mentioned, to provide a measure of the loss of serine, threonine and tyrosine during the hydrolysis. Excess HCl was removed under vacuum at room temperature. Samples and standards were derivatized with phenylisothiocyanate and analyzed according to the PICO-TAG methodology of Waters Associates, Inc. on a Waters HPLC system consisting of a 3.9 mm×15 cm stainless steel PICO-TAG column, two M-510 pumps and a U-6K injector. The effluent stream was monitored at 254 nm by a Waters model 481 LC spectrophotometer. An Apple II computer was used with CHROMATO-CHART, a software product of Interactive Microware, Inc. (State College, Pa. 16804), to record and process data. Cysteine was determined as cysteic acid, by treatment of the enzyme with performic acid prior to hydrolysis (Hirs, 1967b). Tryptophan was estimated spectrophotometrically as described by Edelhoch (1967).

2. Carbohydrate Analysis

Total neutral hexose content was measured by the Winzler (1958) orcinol-sulfuric acid method, as modified by Francis et al. (1962), with mannose as a standard. Aminohexose content was determine by an Elson-Morgan reaction (Rondle and Morgan, 1955; Kraan and Muir, 1957). The sulfhydryl oxidase sample was prepared for this analysis by hydrolysis in 4M HCl at 100° C. for 4 hours, followed by neutralization with NaOH. Determination of 6-deoxyhexose was performed according to the procedure of Dische (1962) except that thioglycolic acid was substituted for cysteine hydrochloride. Assays for sialic acid were performed as described by Warren (1959) after hydrolysis of the enzymes at 80° C. for 60 minutes in 0.1N $H_2SO_4$.

Concentrations of serine, threonine and tyrosine were corrected for destruction by comparison to standard subjected to the hydrolysis procedure. Thereafter, no significant differences in the amino acid composition of sulfhydryl oxidase were noted, as calculated directly from the analyses of hydrolysates from three different preparations of the enzyme. Accordingly, amino acid composition data obtained from the different preparations and hydrolysis times were averaged. Carbohydrate analyses, performed in duplicate, showed the enzyme to contain 21.0% neutral hexose and 1.9% hexosamine by weight; however, the isolated enzyme contained no 6-deoxyhexose or sialic acid. The results of the composition studies are set forth below in Table V.

TABLE V

Chemical Composition of Sulfhydryl Oxidase

| Residue | g per 100 g protein[a] | Residues per 53,000 | Nearest integer |
|---|---|---|---|
| Amino Acids | | | |
| Asx | 10.93 ± 0.49 | 50.4 | 50 |
| Glx | 7.73 ± 0.44 | 31.7 | 32 |
| Ser | 6.42 ± 0.38 | 39.1 | 39 |
| Gly | 4.14 ± 0.41 | 38.5 | 39 |
| His | 1.13 ± 0.25 | 4.4 | 4 |
| Arg | 6.42 ± 0.31 | 21.8 | 22 |
| Thr | 6.20 ± 0.25 | 32.5 | 33 |
| Ala | 3.95 ± 0.07 | 29.4 | 30 |
| Pro | 4.19 ± 0.49 | 22.9 | 23 |
| Tyr | 2.87 ± 0.35 | 9.3 | 9 |
| Val | 6.53 ± 0.25 | 35.0 | 35 |
| Met | 1.47 ± 0.28 | 5.9 | 6 |
| Ile | 3.69 ± 0.44 | 17.3 | 17 |
| Leu | 4.31 ± 0.24 | 20.2 | 20 |
| Phe | 2.54 ± 0.38 | 9.2 | 9 |
| Lys | 2.45 ± 0.17 | 10.1 | 10 |
| Trp[b] | 1.39 ± 0.09 | 4.0 | 4 |
| Cys[c] | 0.54 ± 0.04 | 2.8 | 3 |
| Other | | | |
| hexose | 20.3 | 66.3 | 66 |
| aminohexose | 1.9 | 6.2 | 6 |
| FAD | 1.25 | 0.84 | 1 |

[a]Amino acid percent weights are averages of results from nine data sets. Values for acid-labile amino acids were corrected by comparison to standard subjected to the hydrolysis conditions. Increases in the concentrations of the hydrophobic residues were not observed for long hydrolysis times. Carbohydrate percent weights were determined in duplicate, as describe in the text.
[b]Determined independently by spectrophotometric analysis.
[c]Determined as cysteic acid.

EXAMPLE 7

Determination of Stoichiometry of Reduction of Glutathione by Sulfhydryl Oxidase The ratio of GSH consumed to $H_2O_2$ produced in the course of the catalysis was determined by subjecting preincubated mixtures of GSH and sulfhydryl oxidase to simultaneous assays for reactive sulfhydryl and $H_2O_2$. For these determinations, 0.25 mL of enzyme solution was added to 5 mL of 0.8mM GSH in 40 mM sodium acetate buffer, pH 5.5, and incubated at 37° C. for 15 minutes. Residual sulfhydryl content was then determined as described in the preceding section. Hydrogen peroxide was quantitatively determined by its reaction with a perioxidasecoupled colorimetric reagent. In these analyses, 0.5 mL of the sulfhydryl oxidase/GSH preincubation mixture was diluted into 4.5 mL of the colorimetric reagent, which was prepared immediately before use by combination of the following, per 50 mL of reagent: 19 mL of 0.2M sodium phosphate buffer, pH 8.0; 1 mL of 0.4 mg/mL (590 purpurogallin units) horseradish peroxidase in 50 mM sodium phosphate buffer, pH 7.5; 20 mL of 1.25 mM 4-aminoantipyrine; 10 mL of 0.5% (w/v) phenol. The reaction mixture was incubated for 20 minutes at 37° C., whereafter its absorbance at 500 nm was measured against a blank in which buffer had been substituted for the test material. For preparation of a standard curve for this assay, a nominally 30% (w/v) stock solution of $H_2O_2$ was standardized by titration in cold 1M $H_2SO_4$ with potassium permanganate (Winterton, 1959). Solutions of known peroxide concentrations between 0.1 and 1 mM were prepared from the stock solution and subjected to the assay procedure. These solutions were preincubated in the presence of sulfhydryl oxidase, in the same amount and under the same conditions as were employed in the sample preparation, in order to compensate for possible effects of the enzyme present on either the peroxidase or the colorimetric reagents.

Example 8

Reductive Denaturation and Renaturation of Ribonuclease

Ribonuclease A (Sigma, Type IIIA) was reductively denatured in the presence of 8M urea and 2mercaptoethanol according to the procedure of Anfinsen and Haber (1961), with approximately 40 mg of ribonuclease dissolved in 6 mL of urea solution. Urea was twice recrystallized from hot ethanol, dissolved immediately before use, and the solution was passed over a 1×4 cm Dowes-1 column. Sulfhydryl oxidase was tested for its ability to oxidize the reduced ribonuclease as described by Janolino and Swaisgood (1975), except that the pH of the ribonuclrease incubation mixtures was adjusted to 7.0, the concentration of ribonuclease was 0.45 mg/mL, and the concentrations of sulfhydryl oxidase were 0.11, 0.055 or 0.028 mg/mL. Ribonuclease assays were performed by measuring the decrease in absorbance of a yeast RNA solution (Sigma, type XI) at 258 nm, as described by Dalnitsky et al. (1959). The results of this example are set forth in FIG. 6 and discussed supra.

EXAMPLE 2

Flavin and Stoichiometry

The sulfhydryl apooxidase was prepared by a modification of the guanidine HCl method of Moore et al. (1978). One volume of sulfhydryl oxidase in 0.1M sodium citrate, pH 3.0, was mixed with two volumes of 8M guanidine HCl in the same buffer. After 5 minutes incubation on ice, the mixture was applied to a Sephadex G-25 column, which was equilibrated and eluted with 0.1M sodium phosphate, pH 7.0. All operations were carried out at temperatures of 0° C. to 4° C. The degree of separation was established by examining the absorbance spectrum of the protein-containing fraction. When recovery of the flavin from the guanidine HCl preparation was desired, the pooled flavin-containing fractions were repeatedly batch-extracted with CM cellulose in order to remove guanidinium ion.

In reactivation experiments, freshly prepared apoenzyme was combined with flavin solution and 0.1M sodium phosphate buffer, pH 7.0, in the volume proportions 1:1:2. This mixture was incubated for 14 to 16 hours at 0° C. After the incubation period, the enzyme was separated from excess free flavin by passage through a Pharmacia PD-10 column equilibrated and eluted with 40 mM acetate buffer, pH 5.5.

The flavin component was also extracted from the enzyme by two other methods. Dialyzed sulfhydryl oxidase was boiled for 5 minutes with protection from light and cooled quickly by immersion in ice water. Soluble protein was removed from the supernatant fluid by passage over an Amicon YM-10 ultrafiltration membrane under 40 Psi nitrogen pressure. Alternatively, 0.5 mL of sulfhydryl oxidase in distilled deionized $H_2O$ was made 15% in TCA by addition of 0.315 mL of 40% trichloroacetic acid in three equal aliquots, with 5 minutes incubation time between each addition. After standing for 30 minutes at room temperature, the solution was centrifuged. Trichloroacetic acid was removed from the supernatant liquid by repeated extraction with chloroform.

Quantitative determinations of the concentrations of FAD and FMN solutions were based upon the molar absorptivities of these compounds at 450 nm, 11,300$M^{-1}cm^{-1}$ and 12,200 $M^{-1}$, respectively (Loach, 1970). FAD and FMN were qualitatively distinguished from one another by the fluorometric procedure of Faeder and Siegel (1973), with the use of a Perkin-Elmer MPF-44A fluorescence spectrophotometer. Flavin concentrations in standards and sample preparations were $1 \times 10^{-5}$ to $2 \times 10^{-5}$M.

EXAMPLE 10

Preparation of Freeze Dried A. Niger SHX

A liquid SHX solution containing approximately 3 to 37 U/mL SHX and buffered with about 5 mM citrate with a pH of about 5.5 was poured into trays to a depth of about 20 mm and frozen to about −50 over a period of about 16 hours. The freeze drier chamber was evacuated to about 60 milli Torr, and the material slowly dried until it reached a final temperature of about 30. The condenser temperature was maintained at about −80° C. The freeze drying process took about one week.

BIBLIOGRAPHY

Anfinsen, C. B. & Haber, E. *J. Biol. Chem.* 266:1361 (1961).

Aurbach, G. D. & Jakoby, W. B. *J. Biol. Chem.* 237:565 (1962).

Bessey, O. A., Lowry, O. A. & Love, R. H. *J. Bio. Chem.* 180:755 (1949).

Bradford, M. *Anal. Biochem.* 72:248 (1976).

Cerletti, P. & Siliprandi, N. *Arch. Biochem. Biophys.*, 76:214 (1958).

Chang, T. S. K. & Morton, B. *Biochem. Biophys. Res. Commun.* 66:309 (1975).

Clare, D. A., Blakistone, B. A., Swaisgood, H. E. & Horton, R. H. *Arch. Biochem. Biophys.* 211:44 (1981).

Clare, D. A., Horton, R. H., Stabel, T. J., Swaisgood, H. E. & Lecce, J. G. *Arch. Biochem. Biophys.* 230:138 (1984).

Dische, Z. *Methods Carbohydrate Chem.* 1:477 (1962).

Edelhoch, H. *Biochemistry* 6:1948 (1967).

Ellman, G. L. *Arch. Biochem. Biophys.* 82:70 (1959).

Faeder, E. J. & Siegel, L. M. *Anal. Biochem.* 53:332 (1973).

Francois, C., Marshall, R. D. & Neuberger, A. *Biochem. J.* 88:335 (1962).

Hirs, C. H. W. *Methods Enzymol.* 11:27 (1967a).

Hirs, C. H. W. *Methods Enzymol.* 11:59 (1967b).

Isaacs, C. E., Pascal, T., Wright, C. E. & Gaull, G. E. *Pediatr. Res.* 18:532 (1984).

Janolino, V. G. Sliwkowski, M. X., Swaisgood, H. E. & Horton, H. R. *Arch. Biochem. Biophys.* 91:269 (1978).

Janolino, V. G. & Swaisgood, H. E. *J. Biol. Chem.* 250:2532 (1975).

Kalnitsky, G., Hummel, J. P. & Dierks, C. *J. Biol. Chem.*, 234:1512 (1959).

Kraan, J. G. & Muir, H. *Biochem. J.* 66, 55P (1957).
Laemmli, U. K. *Nature* 227:680 (1970).
Loach, P. A. in "CRC Handbook of Biochemistry, 2nd Edition" (Sober, H. A., Ed.) p. J-32, Chemical Rubber Company, Cleveland, Ohio (1970).
Mandels, G. R. *J. Bacteriol.* 52:230 (1956).
Massey, V., Muller, F., Feldberg, R., Schuman, M., Sullivan, P. A., Howell, L. G., Mayhew, S. G., Matthews, R. G. & Foust, G. P. *J. Biol. Chem.* 244:3999 (1969).
Moore, E. G., Cardemil, E. & Massey, V. *J. Biol. Chem.* 253:6413 (1978).
Morissey, J. H. *Anal. Biochem* 117:307 (1981).
Neufeld, H. A., Green, L. F., Latterell, F. M. & Weintraub, R. L. *J. Biol. Chem.* 232:1093 (1958).
Olsen, J. A. Ph.D. dissertation, University of Iowa (1976).
Ostrowski, M. C. & Kistler, W. C. *Biochemistry* 19:2639 (1980).
Ostrowski, M. C., Kistler, W. S. & Williams-Ashman, H. G. *Biochem. Biophys. Res. Commun.* 87:171 (1979).
Rondle, C. M. J. & Morgan, W. T. J. *Biochem. J.* 61:586 (1955).
Roth, R. A. & Koshland, M. E. *Bio. Chem.* 256:4633 (1981).
Smith, M. H. in "CRC Handbook of Biochemistry, 2nd Edition" (Sober, H. A., Ed.), p. C-30, Chemical Rubber Company, Cleveland, Ohio (1967).
Takamuri, K., Thorpe, J. M. & Goldsmith, L. A. *Biochem. Biophys. Acta* 615:309 (1980).
Warren, L. *J. Biol. Chem.* 234:1971 (1959).
Winterton, R. J. in "Comprehensive Analytical Chemistry Vol. 18" (Wilson, C. L. & Wilson, D. W., Eds.) pp. 238, Elsevier, Amsterdam (1959).
Winzler, R. J. *Ciba Found. Symp. Chem. Biol. Mucopolysaccharides,* 245 (1958).
Young, J. D. & Nimmo, I. A. *Biochem. J.* 130:33P (1972).
Yphantis, D. A. *Biochemistry* 3:297 (1964).

The foregoing general discussion and experimental examples are intended to be illustrative of the present invention, and are not to be considered as limiting. Other variations within the spirit and scope of this invention are possible and will present themselves to those skilled in the art.

We claim:

1. An isolated microbial sulfhydryl oxidase which is a flavoprotein and is characterized by a pH optimum of about 5.5 for the oxidation of glutathione in an acetate buffer at 25 degrees Centigrade, absorbance maxima at about 442.5 nanometers, 364.5 nanometers and 274 nanometers, and a molecular weight of about 106,000 as determined by equilibrium sedimentation; said sulfhydryl oxidase being constituted by subunits with a molecular weight of about 50,000 to about 55,000 as determined by SDS polyacrylamide gel eletrophoresis.

2. The isolated microbial sulfhydryl oxidase of claim 1 wherein said enzyme is a glycoprotein.

3. The isolated microbial sulfhydryl oxidase of claim 1 wherein said enzyme is derived from *Aspergillus niger.*

4. The isolated microbial sulfhydryl oxidase of claim 1 wherein said enzyme has a pH optimum in the range of about 6 to about 7 for the oxidation of glutathione in a sodium phosphate buffer.

5. A stable enzyme preparation which comprises a microbially derived sulfhydryl oxidase which is a flavoprotein, a buffer, and ammonium sulfate in sufficient concentrations to provide an aqueous suspension of sulfhydryl oxidase.

6. The stable enzyme preparation of claim 5 wherein said sulfhydryl oxidase is derived from *Aspergillus niger.*

7. A stable freeze-dried enzyme preparation which comprises a microbial sulfhydryl oxidase which is a flavoprotein.

8. The stable freeze-dried enzyme preparation of claim 7 wherein said sulfhydryl oxidase is derived from *Aspergillus niger.*

9. A method for the recovery of sulfhydryl oxidase which is a flavoprotein from a microbial source which comprises the steps of:
cultivating a sulfhydryl oxidase-producing strain of a mold in a nutrient medium;
recovering sulfhydryl oxidase from the cells of said mold (medium); and
purifying the resulting sulfhydryl oxidase.

10. The method in accordance with claim 9 wherein said recovery of the sulfhydryl oxidase is carried out by suspending the mold in a brine solution of sufficient strength to partition the enzyme into the brine solution.

11. The method in accordance with claim 9 wherein said recovery of the sulfhydryl oxidase is carried out by enzymatic treatment of the mold.

12. The method in accordance with claim 9 wherein said mold is *Spergillus niger.*

13. The method in accordance with claim 9 wherein the sulfhydryl oxidase is purified by organic solvent fractionation and chromatography.

14. The method of claim 9 wherein said sulfhydryl oxidase which is a flavoprotein is further characterized by a pH optimum of about 5.5 for the oxidation of glutathione in an acetate buffer at 25 degrees Centigrade, absorbance maximum at about 442.5 nanometers, 364.5 nanometers and 247 nanometers, and a molecular weight of about 106,000 as determined by equilibrium sedimentation; said sulfhydryl oxidase being constituted by subunits with a molecular weight of about 50,000 to about 55,000 as determined by SDS polyacrylylamide gel electrophoresis.

* * * * *